United States Patent [19]

Beck et al.

[11] 4,180,568

[45] Dec. 25, 1979

[54] CONTROL OF PHYTOPATHOGENS WITH CERTAIN 2,6-DINITROANILINES

[75] Inventors: James R. Beck, Indianapolis; Joseph A. Yahner, New Palestine, both of Ind.

[73] Assignee: Eli Lilly and Company, Indianapolis, Ind.

[21] Appl. No.: 878,370

[22] Filed: Feb. 16, 1978

Related U.S. Application Data

[60] Division of Ser. No. 719,299, Aug. 31, 1976, Pat. No. 4,091,096, which is a continuation-in-part of Ser. No. 668,360, Mar. 19, 1976, abandoned, which is a continuation-in-part of Ser. No. 589,312, Jun. 23, 1975, abandoned.

[51] Int. Cl.$^2$ ............................................. A01N 9/20
[52] U.S. Cl. .................................................. 424/226
[58] Field of Search ......................... 424/226; 260/349

[56] References Cited

U.S. PATENT DOCUMENTS

| 3,764,624 | 10/1973 | Strong et al. | 71/121 |
| 3,877,924 | 4/1975 | Fischer | 71/121 |
| 3,948,957 | 4/1976 | Beck | 260/349 |
| 4,065,559 | 12/1977 | Froyd | 424/226 |

Primary Examiner—V. D. Turner
Attorney, Agent, or Firm—Dwight E. Morrison; Everet F. Smith

[57] ABSTRACT

It has been discovered that fungal foliar phytopathogens may be controlled by the use of a broad class of 2,6-dinitroanilines. The fungicidally-effective compounds may bear a broad range of substituent groups on the anilino nitrogen and in the 3- and 4-positions of the benzene ring.

7 Claims, No Drawings

CONTROL OF PHYTOPATHOGENS WITH CERTAIN 2,6-DINITROANILINES

CROSS REFERENCE

This application is a division of our then copending application Ser. No. 719,299, filed Aug. 31, 1976, now U.S. Pat. No. 4,091,096 (May 23, 1978), which was a continuation-in-part of our then copending application Ser. No. 668,360, filed Mar. 19, 1976, now abandoned, which was a continuation-in-part of our then copending application Ser. No. 589,312, filed June 23, 1975, now abandoned.

BACKGROUND OF THE INVENTION

1. Field of the Invention

This invention relates to the control of plant pathogens. More particularly, this invention relates to the control of fungal foliar phytopathogens, especially downy mildew and late blight, using a broad class of 2,6-dinitroanilines.

2. Description of the Prior Art

Beginning in the early 1960's, Soper disclosed that 2,6-dinitroanilines possess herbicidal activity, most notably preemergent herbicidal activity. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939. See also U.S. Pat. No. 3,725,479, for intermediate compounds.

Malichenko et al., Fiziol. Aktiv. Veschestva 1969, 2, 75-8; C.A. 73, 13451e (1970), disclose that some 2,6-dinitroanilines bearing a trifluoromethyl group in the 4-position possess some activity against *Phytophthora infestans*, the causative organism of late blight of tomatoes.

Clark et al., U.S. Pat. No. 3,119,736, disclose a broad class of compounds alleged to be fungicides. The generic description of such compounds includes dinitroanilines, but there is no specific disclosure of 2,6-dinitroanilines.

Zsolnai, *Biochemical Pharmacology* 5, 287-304 (1961), discloses that certain 2,4-dinitroanilines possess some fungicidal activity against various organisms. No 2,6-dinitroaniline was disclosed, nor was *Plasmopara viticola* among the organisms against which activity was shown.

Buczacki, *Ann. Appl. Biol.* 75, 25 (1973), tested five dinitroanilines against clubroot of cabbage with variable results. He concluded, however, that "dinitroanilines are unlikely to be of value in the control of clubroot."

Eshel and Katan, *Weed Science* 20, 243 (1972), observed the effects of four dinitroanilines against *Rhizoctonia solani* and *Fusarium oxysporum*. Three of the four test compounds decreased the growth of *R. solani* at the highest rates tested, but none of the four appreciably decreased the growth of *F. oxysporum* at any rate tested.

A study of trifluralin-treated soil by Breazeale and Camper, *Appl. Microbiol.* 19, 379 (1970), indicated that the actinomycete population increased as compared to the control, while the population of bacteria and fungi decreased.

A discussion of tests against the fungus *Lagenidium callinectes* is presented by Bland et al. in a paper entitled "Chemical Control of Lagenidium", an SEA Grant Publication UNC-SG-76-02, March 1976. The publication shows that some control of the fungus, which is a parasite of marine crustacea, is accomplished by application of TREFLAN (trifluralin) to water in which spores of the fungus were growing.

SUMMARY OF THE INVENTION

The present invention is a method for reducing the incidence and severity of fungal foliar phytopathogens. Use of the method for the control of downy mildew and of late blight are preferred embodiments of the invention. The method is performed by applying to the foliage of the host plant a fungicidally-effective amount of a 2,6-dinitroaniline selected from the class consisting of compounds having the following formulae:

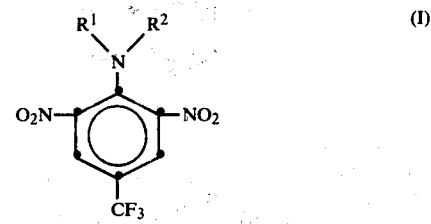

wherein
$R^1$ is H, $C_2$-$C_3$ alkyl, chloroethyl, cyanoethyl, $C_3$-$C_4$ alkenyl or halo $C_3$-$C_4$ alkenyl;

when $R^1$ is H, $R^2$ is $N(R^3)_2$, normal $C_3$-$C_6$ alkyl, branched $C_4$-$C_7$ alkyl containing no tertiary carbon atoms, 1-hydroxy-2-propyl, methallyl, N-ethyl-3-piperidyl, 2,6-dimethyl-1-piperidyl, 2,5-dimethylpyrrolidino or 2-ethyl-1-piperidyl;

when $R^1$ is not H, $R^2$ is 3-chloro-n-butyl, $C_3$-$C_4$ alkenyl, halo $C_3$-$C_4$ alkenyl, chloroethyl, cyclopropylmethyl, cyanoethyl, hydroxyethyl, n-$C_3H_7$, or epoxypropyl;

each $R^3$ is independently $C_1$-$C_3$ alkyl;

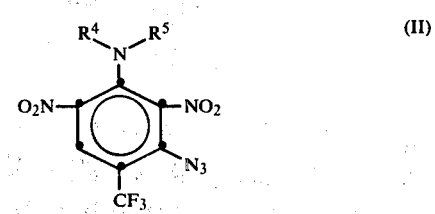

wherein
$R^4$ is H or $C_1$-$C_3$ alkyl;

when $R^4$ is H, $R^5$ is $N(R^6)_2$, $C_1$-$C_7$ normal or branched alkyl containing no tertiary carbon atoms, $C_3$-$C_4$ alkenyl or N-methyl-2-propionamido;

when $R^4$ is $C_1$-$C_3$ alkyl, $R^5$ is $C_1$-$C_4$ alkyl or $C_3$-$C_4$ alkenyl; and each $R^6$ is independently $C_1$-$C_3$ alkyl;

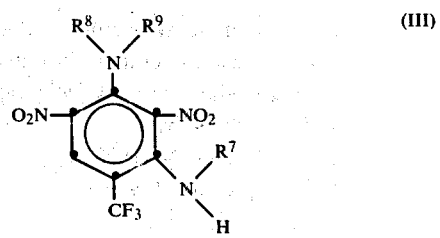

wherein $R^7$ is H, CN, $C_1$–$C_3$ alkyl or $C_2$–$C_3$ alkanoyl;

$R^8$ is H or $C_1$–$C_3$ alkyl;

when $R^8$ is H, $R^9$ is $N(R^{10})_2$, $C_1$–$C_6$ normal or branched alkyl containing no tertiary carbon atoms, or $C_3$–$C_4$ alkenyl;

when $R^8$ is $C_1$–$C_3$ alkyl, $R^9$ is $C_1$–$C_3$ alkyl, halo $C_3$–$C_4$ alkenyl, propargyl, tetrahydrofurfuryl or $C_3$–$C_4$ alkenyl; and each $R^{10}$ is independently $C_1$–$C_3$ alkyl;

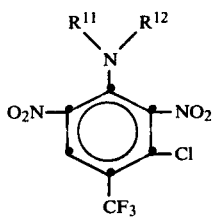

(IV)

wherein $R^{11}$ is H or $C_1$–$C_3$ alkyl;

when $R^{11}$ is H, $R^{12}$ is $N(R^{13})_2$, $C_1$–$C_4$ normal or branched alkyl containing no tertiary carbon atoms, or $C_3$–$C_4$ alkenyl;

when $R^{11}$ is $C_1$–$C_3$ alkyl, $R^{12}$ is $C_1$–$C_3$ alkyl or $C_3$–$C_4$ alkenyl; and each $R^{13}$ is independently $C_1$–$C_3$ alkyl;

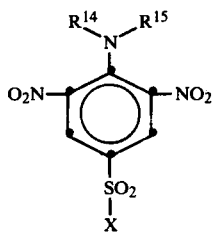

(V)

wherein

X is $N(R^{16})_2$, chloro, $CH_3$, $N=S(R^{17})_2$, $N(R^{18})CH_2Het$, $C_1$–$C_2$ alkoxy, $N=CHN(CH_3)_2$, $N=C(R^{19})OR^{20}$, $N=CHOR^{21}$ or $N_3$;

$R^{14}$ is H, $C_3$–$C_4$ alkenyl or $C_1$–$C_4$ alkyl; when $R^{14}$ is H, $R^{15}$ is $C_3$–$C_7$ secondary alkyl;

when $R^{14}$ is not H, $R^{15}$ is $C_1$–$C_5$ alkyl, cyclopropylmethyl, $C_5$–$C_6$ cycloalkyl, $C_3$–$C_4$ alkenyl, halo $C_2$–$C_3$ alkyl or halo $C_3$–$C_4$ alkenyl;

one of $R^{16}$ is H or $CH_3$ and the other is H, $SCCl_3$, $CH_3$, phenylthio, OH, $C_1$–$C_4$ alkoxy or $NH_2$;

each $R^{17}$ is independently $C_1$–$C_2$ alkyl, phenyl or benzyl;

Het is 2,5-dimethylpyrrolidino, piperidino, morpholino, $C_1$–$C_2$ alkylpiperidino, hexahydroazepino, 2,2-dimethylaziridino, or $C_1$–$C_2$ alkylpiperazino;

$R^{18}$ is H or methyl;

$R^{19}$ is $C_1$–$C_2$ alkyl or phenyl;

$R^{20}$ is $C_1$–$C_4$ alkyl; and $R^{21}$ is $C_1$–$C_2$ alkyl;

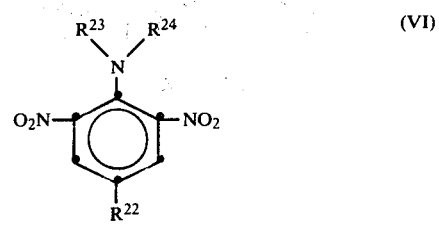

(VI)

wherein $R^{22}$ is cyano $C_1$–$C_3$ alkyl, halo or $C_1$–$C_4$ alkyl;

$R^{23}$ is H, chloroethyl, hydroxyethyl or $C_1$–$C_4$ nontertiary alkyl; and when $R^{23}$ is H, $R^{24}$ is $C_3$–$C_7$ secondary alkyl;

when $R^{23}$ is not H, $R^{24}$ is $C_1$–$C_4$ nontertiary alkyl, chloroethyl, hydroxyethyl, halo $C_3$–$C_4$ alkenyl or $C_3$–$C_4$ alkenyl;

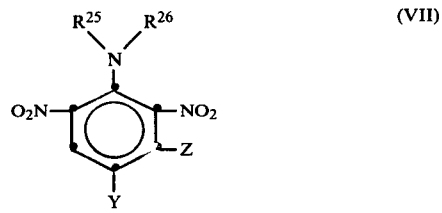

(VII)

wherein

Y is H or $CH_3$;

Z is $NH_2$, $SCH_2CN$, Cl, $CH_3$ or $OCH_3$;

$R^{25}$ is H or $C_2$–$C_4$ nontertiary alkyl; and when $R^{25}$ is H, $R^{26}$ is $C_3$–$C_7$ secondary alkyl or N-methyl-2-propionamido;

when $R^{25}$ is $C_2$–$C_4$ nontertiary alkyl, $R^{26}$ is $C_2$–$C_4$ nontertiary alkyl or $C_3$–$C_4$ alkenyl;

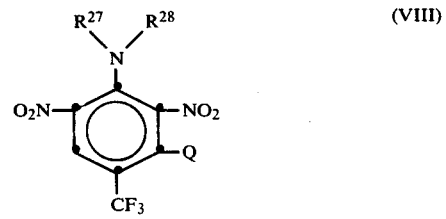

(VIII)

wherein

Q is OH, $OCH_3$, $SCH_3$, SCN, $SCH_2CH_2CN$, $SCH_2CN$, $SCH_2CO_2CH_3$, $CO_2H$, $CONH_2$ or CN;

$R^{27}$ is H or $C_1$–$C_3$ alkyl; and when $R^{27}$ is H, $R^{28}$ is $N(CH_3)_2$ or $C_1$–$C_6$ normal or branched alkyl containing no tertiary carbon atoms; and when $R^{27}$ is $C_1$–$C_3$ alkyl, $R^{28}$ is propargyl, tetrahydrofurfuryl or $C_1$–$C_4$ nontertiary alkyl;

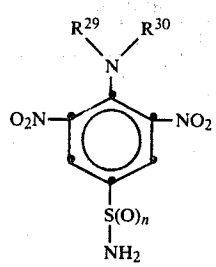
(IX)

wherein
R$^{29}$ is hydrogen, C$_3$–C$_4$ alkenyl or C$_1$–C$_3$ alkyl;
when R$^{29}$ is hydrogen, R$^{30}$ is C$_3$–C$_7$ secondary alkyl;
when R$^{29}$ is not hydrogen, R$^{30}$ is C$_1$–C$_4$ alkyl; and n is 0 or 1.

A particularly preferred embodiment of the invention is the method for reducing the incidence and severity of grape downy mildew which comprises applying to the foliage of the host plant a fungicidally-effective amount of a compound described above.

Another particularly preferred embodiment is the method for reducing the incidence and severity of tomato late blight which comprises applying to the foliage of the host plant a fungicidally-effective amount of a dinitroaniline compound of the formula

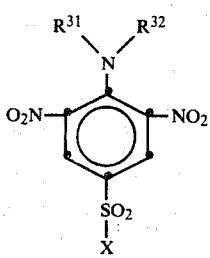

wherein
X' is N(R$^{33}$)$_2$, chloro, CH$_3$, N=S(R$^{34}$)$_2$, N(R$^{35}$)CH$_2$Het', C$_1$–C$_2$ alkoxy, N=CHN(CH$_3$)$_2$, N=C(R$^{36}$)OR$^{37}$, N=CHOR$^{38}$ or N$_3$;
R$^{31}$ is H, C$_3$–C$_4$ alkenyl or C$_1$–C$_4$ alkyl;
when R$^{31}$ is H, R$^{32}$ is C$_3$–C$_7$ secondary alkyl;
when R$^{31}$ is not H, R$^{32}$ is C$_1$–C$_5$ alkyl, cyclopropylmethyl, C$_5$–C$_6$ cycloalkyl, C$_3$–C$_4$ alkenyl, halo C$_2$–C$_3$ alkyl or halo C$_3$–C$_4$ alkenyl;
one of R$^{33}$ is H or CH$_3$ and the other is H, SCCl$_3$, CH$_3$, phenylthio, OH, C$_1$–C$_4$ alkoxy or NH$_2$;
each R$^{34}$ is independently C$_1$–C$_2$ alkyl, phenyl or benzyl;
Het' is 2,5-dimethylpyrrolidino, piperidino, morpholino, C$_1$–C$_2$ alkylpiperidino, hexahydroazepino, 2,2-dimethylaziridino, or C$_1$–C$_2$ alkylpiperazino;
R$^{35}$ is H or methyl;
R$^{36}$ is C$_1$–C$_2$ alkyl or phenyl;
R$^{37}$ is C$_1$–C$_4$ alkyl; and
R$^{38}$ is C$_1$–C$_2$ alkyl.

It will be noted that the above formula is equivalent to Formula V above.

DESCRIPTION OF THE PREFERRED EMBODIMENT

For the most part, the 2,6-dinitroanilines useful in the method of this invention are compounds known in the herbicide art. Exceptions to this general rule are the 3-azido compounds of Formula II; the cyanamines of Formula III; the cyanomethylthio compound of Formula VII; some of the sulfur-containing compounds of Formula VIII; and the sulfenamides and sulfinamides of Formula IX, all of which are new compounds first synthesized by us.

Those compounds useful in this invention which are known in the herbicide art are prepared by methods described in the various patents listed in the prior art section of this specification and all of which are incorporated herein by reference. Since the preparative procedures described in such patents are sufficient to allow those skilled in the art to prepare the compounds, no attempt will be made here to further describe the preparation of such compounds.

The 3-azido compounds of Formula II, the cyanamines of Formula III and the sulfur-containing compounds of Formula VIII are prepared from the corresponding 3-chloro compounds. The 3-chloro compounds are intermediates in the preparation of the 1,3-phenylenediamines of U.S. Pat. No. 3,617,252 and the 3-alkoxy and alkylthio compounds of U.S. Pat. No. 3,764,624 and the preparation of the 3-chloro intermediates is described in both such patents.

The 3-azido compounds are prepared, for example, by the reaction of the corresponding 3-chloro compound with an alkali metal azide such as sodium azide in the presence of an inert solvent such as dimethylformamide. The reaction is conveniently run at room temperature. The 3-thiocyanato compounds are prepared in a similar manner employing an alkali metal sulfide such as sodium sulfide and cyanogen chloride. Compounds bearing a cyanomethylthio group in the 3-position are prepared from the corresponding 3-chloro compound by reaction with sodium sulfide and chloroacetonitrile. The other sulfur-containing compounds are prepared by reaction of the 3-chloro compound with the appropriate mercapto compound in the presence of an alkali metal hydroxide such as lithium hydroxide or potassium hydroxide. The cyanamines are prepared by heating the 3-chloro intermediate with cyanamide in the presence of a tertiary amine such as triethylamine.

While it is believed that those skilled in the art can prepare all the compounds useful in the present invention, the following preparative examples are given to insure that the novel compounds described above can be readily prepared.

EXAMPLE 1

A solution of 2.3 g. of sodium azide in 15 ml. of water was added dropwise to a solution of 7 g. of 3-chloro-N,N-dimethyl-2,6-dinitro-4-trifluoromethylaniline in 90 ml. of dimethylformamide at room temperature. The mixture was stirred at room temperature for one hour, poured over icewater and filtered to recover 6.9 g. (94%) of 3-azido-N,N-dimethyl-2,6-dinitro-4-trifluoromethylaniline, m.p. 66°–67° C. The structure was confirmed by the NMR and IR spectra and elemental analysis.

Calculated: C, 33.76; H, 2.20; N, 26.25: Found: C, 33.98; H, 2.19; N, 26.53.

EXAMPLE 2

A solution of 0.75 g. of sodium azide in 15 ml. of water was added dropwise to a solution of N-n-butyl-3-chloro-2,6-dinitro-N-ethyl-4-trifluoromethylaniline in 75 ml. of dimethylformamide at room temperature. The mixture was stirred at room temperature for 2 hours and poured over ice-water. The product separated as an oil.

The mixture was extracted three times with methylene chloride, the methylene chloride was evaporated, the residue taken up in ether, and the ether solution extracted three times with water. Evaporation of the ether left 3.1 g. (92%) of 3-azido-N-n-butyl-2,6-dinitro-N-ethyl-4-trifluoromethylaniline as an oil. The structure was confirmed by the NMR and IR spectra and elemental analysis.

Calculated: C, 41.49; H, 4.02; N, 22.33: Found: C, 41.39; H, 3.89; N, 22.10.

EXAMPLE 3

A solution of 1.0 g. of sodium azide in 10 ml. of water was added dropwise to a solution of 3.2 g. of N-(3-chloro-2,6-dinitro-4-trifluoromethylphenyl)-N',N'-dimethylhydrazine in 80 ml. of dimethylformamide at room temperature. The mixture was stirred at room temperature for one hour, poured over ice-water and filtered. The solid product was dried and recrystallized from 2B ethanol to yield 3.1 g. (93%) of N-(3-azido-2,6-dinitro-4-trifluoromethylphenyl)-N',N'-dimethylhydrazine, m.p. 123°–125° C. The structure was confirmed by the NMR and IR spectra and elemental analysis.

Calculated: C, 32.25; H, 2.41; N, 29.25; Found: C, 32.21; H, 2.39; N, 29.34. Following the procedure of Example 1, 2 or 3, the following additional compounds of Formula II were prepared.

| $R^4$ | $R^5$ | Melting Point, °C. |
|---|---|---|
| $C_2H_5$ | $C_2H_5$ | Oil |
| H | $CH(CH_3)C_3H_7$ | Oil |
| H | $CH(CH_3)C_2H_5$ | 77–78 |
| H | $CH[CH(CH_3)_2]_2$ | Oil |
| H | $CH(C_2H_5)C_3H_7$ | 27–28 |
| H | $CH_3$ | 118–120 |
| $C_2H_5$ | $n-C_3H_7$ | Oil |
| H | $CH(C_2H_5)_2$ | 77–79 |
| $n-C_3H_7$ | $n-C_3H_7$ | Oil |
| H | $CH(CH_3)CONHCH_3$ | 163, dec. |
| H | $n-C_3H_7$ | 70–72 |
| $C_2H_5$ | methallyl | 46–48 |

EXAMPLE 4

A solution of 40 g. of 3-chloro-2,6-dinitro-N-(3-pentyl)-4-trifluoromethylaniline, 10.5 g. of cyanamide and 30 g. of triethylamine in 250 ml. of 3A ethanol was heated under reflux for 5 days. The solution was allowed to cool and was then poured over ice-water. The product which separated was recrystallized from 3A ethanol-water to give 36 g. (71%) of 3-cyanamino-2,6-dinitro-N-(3-pentyl)-4-trifluoromethylaniline, triethylamine salt, m.p. 135°–137° C. The structure was confirmed by the NMR and IR spectra and elemental analysis.

Calculated: C, 49.35; H, 6.32; N, 18.17; Found: C, 49.56; H, 6.06; N, 18.37. Following the procedure of Example 4, the following additional compounds of Formula III were prepared. All were obtained as the triethylamine salt.

| $R^7$ | $R^8$ | $R^9$ | Melting Point, °C. |
|---|---|---|---|
| CN | $n-C_3H_7$ | $n-C_3H_7$ | 102–103 |
| CN | $C_2H_5$ | $C_2H_5$ | 122–124 |
| CN | H | $n-C_3H_7$ | 130–131 |
| CN | $CH_3$ | $C_2H_5$ | 84–86 |

-continued

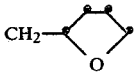

| $R^7$ | $R^8$ | $R^9$ | Melting Point, °C. |
|---|---|---|---|
| CN | $CH_3$ | (cyclopropylmethyl-O) | 98–100 |
| CN | $CH_3$ | $CH_2C\equiv CH$ | 129–132 |
| CN | $n-C_3H_7$ | $CH_2C=CH_2$, Cl | 68–70 |

The following cyanamino free bases were prepared by neutralizing the corresponding triethylamine salts with dilute hydrochloric acid in diethyl ether at room temperature.

| $R^7$ | $R^8$ | $R^9$ | Melting Point, °C. |
|---|---|---|---|
| CN | $C_2H_5$ | $C_2H_5$ | 195–198 |
| CN | H | $CH(C_2H_5)_2$ | 106–110 |
| CN | H | $n-C_3H_7$ | 140–143 |

EXAMPLE 5

To a cold solution of 40 g. of 3-chloro-2,6-dinitro-N-(3-pentyl)-4-trifluoromethylaniline in 400 ml. of dimethylformamide was added 36 g. of sodium sulfide nonahydrate in 100 ml. of water. The mixture was stirred for one-half hour and cyanogen chloride was bubbled into the cold solution for 10 minutes. The dark solution became light red. The reaction mixture was poured over ice-water and the solid product separated. Recrystallization from 3A ethanol-water gave 39 g. (89%) of 2,6-dinitro-N-(3-pentyl)-3-thiocyanato-4-trifluoromethylaniline, m.p. 97°–99° C. The structure was confirmed by the NMR spectrum and elemental analysis.

Calculated: C, 41.27; H, 3.46; N, 14.81; Found: C, 41.02; H, 3.40; N, 14.56. Following the procedure of Example 5, the following additional compounds of Formula VIII were prepared.

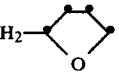

| Q | $R^{23}$ | $R^{24}$ | Melting Point, °C. |
|---|---|---|---|
| SCN | H | $CH_3$ | 125–126 |
| SCN | $CH_3$ | $CH_3$ | 153–155 |
| SCN | H | $N(CH_3)_2$ | 146–148 |
| SCN | $n-C_3H_7$ | $n-C_3H_7$ | Oil |
| SCN | $C_2H_5$ | $C_2H_5$ | 116–118 |
| SCN | $CH_3$ | (cyclopropylmethyl-O) | 75–76 |
| SCN | $CH_3$ | $CH_2C\equiv CH$ | 84–86 |
| SCN | $C_2H_5$ | $CH_2C=CH_2$, $CH_3$ | 92–94 |

The preparation of 3-cyanomethylthio compounds is illustrated by the following example.

EXAMPLE 6

A mixture of 3.4 g. of 3-chloro-N,N-diethyl-2,6-dinitro-4-trifluoromethylaniline and 2.4 g. of sodium sulfide nonahydrate in dimethyl sulfoxide was stirred for one hour at 0° C. Chloroacetonitrile (0.76 g.) was added and the mixture was stirred overnight at room temperature. The reaction mixture was poured over ice and extracted with ether. The ether was evaporated and the residue was recrystallized twice from ethanol to yield 2.7 g. of 3-cyanomethylthio-N,N-diethyl-2,6-dinitro-4-trifluoromethylaniline, m.p. 77°–79° C. The structure was confirmed by the NMR spectrum.

EXAMPLE 7

To a cold solution of 3.6 g. of 3-chloro-2,6-dinitro-N-(3-pentyl)-4-trifluoromethylaniline and 1.1 g. of methyl thioglycolate in 75 ml. of dimethylformamide was added dropwise 6.6 g. of potassium hydroxide in 5 ml. of water. The mixture was allowed to come to room temperature and stirred for one hour. The reaction mixture was poured over ice water and the product solidified. It was recovered by filtration and recrystallized from ethanol to yield 1.6 g. of 2,6-dinitro-N-(3-pentyl)-3-methoxycarbonylmethylthio-4-trifluoromethylaniline, m.p. 60°–61° C. The structure was confirmed by the NMR spectrum and elemental analysis.

Calculated: C, 42.35; H, 4.27; N, 9.88; Found: C, 42.43; H, 4.14; N, 9.89.

EXAMPLE 8

To a cold solution of 6.0 g. of 3-chloro-2,6-dinitro-N-methyl-4-trifluoromethylaniline and 4.0 ml. of β-mercaptopropionitrile in 100 ml. of dimethylformamide was added portionwise, with stirring 0.6 g. of lithium hydroxide. The solution was warmed to 25° C. and stirred for 12 hours. The reaction mixture was poured over ice water and the product solidified. It was recovered by filtration and recrystallized from ethanol to yield 5.8 g. of 3-cyanoethylthio-2,6-dinitro-N-methyl-4-trifluoromethylaniline, m.p. 116°–117° C. The structure was confirmed by the NMR spectrum and elemental analysis.

Calculated: C, 37.72; H, 2.59; N, 16.00; Found: C, 37.96; H, 2.84; N, 16.29.

EXAMPLE 9

To a cold solution of 21.3 g. of 3-chloro-2,6-dinitro-N-(3-pentyl)-4-trifluoromethylaniline and 10 ml. of β-mercaptopropionitrile in 200 ml. of dimethylformamide was added portionwise 2.0 g. of lithium hydroxide. The mixture was warmed to 25° C. and stirred for 2 hours. The reaction mixture was poured over ice water and the product oiled out. The solution was extracted with ether, washed with water, dried and concentrated to leave an oil. The product was chromatographed on a silica-gel column with benzene and the solvent was removed to yield 2.0 g. of 3-cyanoethylthio-2,6-dinitro-N-(3-pentyl)-4-trifluoromethylaniline. The structure was confirmed by the NMR spectrum and elemental analysis.

Calculated: C, 44.33; H, 4.22; N, 13.79; Found: C, 44.29; H, 4.22; N, 13.63.

EXAMPLE 10

To a cold solution of 1.7 g. (0.01 mole) of silver nitrate in 150 ml. of methanol there was added portionwise 6.0 g. (0.01 mole) of bis[4-di(n-propyl)amino-3,5-dinitrophenyl]disulfide [prepared as taught by Cannon, U.S. Pat. No. 3,725,479 (Apr. 3, 1973)]. When the addition was complete, gaseous ammonia was bubbled into the solution for about 4 hours and an additional 0.5 g. of silver nitrate was added. Thin layer chromatography showed that there was a slight amount of starting material still remaining. The reaction mixture was stirred overnight at room temperature. The reaction mixture was then cooled and concentrated in vacuo. The residue was taken up in benzene and filtered. The solid material collected on the filter was washed with ether. The filtrate was concentrated in vacuo to leave a red oil, which solidified. The product weighed 2.4 g. and had a melting point of about 63°–65° C. It was identified by elemental analyses and NMR and IR spectra as 4-(dipropylamino)-3,5-dinitrobenzene sulfenamide.

Calculated: C, 45.85; H, 5.77; N, 17.82; S, 10.20; Found: C, 45.59; H, 5.50; N, 17.62; S, 9.90.

EXAMPLE 11

To a solution of 1 g. (0.003 mole) of 4-(dipropylamino)-3,5-dinitrobenzenesulfenamide in 50 ml. of methylene chloride, there was added 0.56 g. (0.0032 mole) of m-chloroperbenzoic acid. The reaction mixture became slightly warm and it was stirred for about 15 minutes at ambient room temperature. Thin layer chromatography showed no starting material remained. The reaction product mixture was extracted twice with dilute aqueous sodium bicarbonate solution and then washed once with water. The washings were discarded and the organic layer was concentrated in vacuo to leave an oil which was eluted from a silica gel column with 1:1 ethyl acetate:hexane solvent. The first product obtained from the column was a disulfide compound. The second product isolated from the column was recrystallized from 95 percent ethanol to yield product having a melting point of about 125°–126° C., and was identified by elemental analyses and NMR spectrum as 4-(dipropylamino)-3,5-dinitrobenzenesulfinamide. Weight: 550 mg.

Calculated: C, 43.63; H, 5.49; N, 16.96; Found: C, 43.89; H, 5.31; N, 16.68.

EXAMPLE 12

A mixture of 5.5 g. (0.02 mole) of 4-bromo-2,6-dinitroanisole and 5 ml. of 3-aminopentane was stirred at room temperature for about 4 hours. At the end of that time, thin layer chromatography showed no starting material remained. The reaction product mixture was cooled over the weekend in the refrigerator and then concentrated in vacuo to leave a residual oil, which solidified on standing. This product was identified by elemental analyses and NMR spectrum as 4-bromo-N-(1-ethylpropyl)-2,6-dinitroaniline. Weight: 7.0 g.

Calculated: C, 39.78; H, 4.25; N, 12.65; Found: C, 40.05; H, 4.18; N, 12.85.

EXAMPLE 13

To a cold solution of 5.0 g. of 3-chloro-2,6-dinitro-N-(3-pentyl)-4-trifluoromethylaniline in 75 ml. of dimethylformamide was added 10 ml. of methylmercaptan. To the mixture was then added a solution of 5.0 g. of potassium hydroxide in 20 ml. of water portionwise. The reaction mixture was warmed to ambient room temperature and stirred for about ½ hour. The reaction mixture was then poured over a mixture of ice and water. The precipitate which separated crystallized on standing overnight. The precipitate was filtered off and dried. It had a melting point of about 39°–41° C. and was identified by elemental analyses and NMR spectrum as 2,6-dinitro-N-(3-pentyl)-3-methylmercapto-4-trifluoromethylaniline. The product weighed 4.0 g.

Calculated: C, 42.51; H, 4.39; N, 11.44; Found: C, 42.59; H, 4.31; N, 11.29.

EXAMPLE 14

To a cold solution (0° C.) of 3.5 g. of 3-chloro-2,6-dinitro-N,N-diethylaniline in 60 ml. of dimethylformamide, there was added dropwise a solution of 3.4 g. of sodium monosulfide nonahydrate in 10 ml. of water. After addition was complete, thin layer chromatography of the reaction mixture showed little starting material remained. There was then added to the reaction mixture an excess of chloroacetonitrile at room temperature. The reaction mixture was stirred at room temperature for about 6 hours and then poured over crushed ice. The aqueous mixture was filtered and the solid which was recovered was chromatographed over a silica gel column using benzene as the eluent. There was isolated product having a melting point of about 63°–65° C. and identified by elemental analyses and NMR spectrum as [[3-(diethylamino)-2,4-dinitrophenyl]thio]acetonitrile.

Calculated: C, 46.44; H, 4.55; N, 18.05; Found: C, 46.29; H, 4.30; N, 18.05.

Tests against fungal foliar phytopathogens have demonstrated the powerful plant protective effect of the compounds of this invention. The first series of tests to be described exemplify the use of the compounds to reduce both the incidence and severity of grape downy mildew. In the tests described below, the compounds were applied as a solution or emulsion prepared by mixing 70 mg. of test compound with 1.925 ml. of a mixture prepared from 500 ml. of acetone, 500 ml. of ethanol and 100 ml. of polyoxyethylene sorbitan monolaurate. The composition containing the test compound was then diluted with deionized water to obtain the desired concentration, measured in parts per million by weight (ppm.).

In the tests, the host plant was *Vitis vinifera*. The pathogen employed was *Plasmopara viticola*. Stock grape plants were grown in a greenhouse to serve as a supply of leaves for test use. On the test day, young expanding leaves were detached from the vines. One leaf was placed bottom side up in a plastic petri plate (100×20 mm.) and a water-soaked wad of cotton was wrapped around the petiole base. The petri plate contained a Whatman filter paper placed on top of an expanded plastic mat. The mat and filter paper kept the leaf above water flooding the bottom of the petri plate. Each test chemical was sprayed on the under side of the leaf and allowed to dry. All the test leaves were then inoculated by atomizing a conidial suspension over the under leaf surface and then each plate was covered. All the plates were placed on a shelf in a mist room at a temperature of 18°–20° C. and a light/dark cycle of 8/16 hours. Illumination was obtained from cool white fluorescent lamps ranging between 850–1000 foot-candles. Seven days after treatment, the leaves were examined and symptoms of disease were observed and results recorded using a scale of 1 to 5, wherein 1 indicates severe disease or no control and 5 indicates no disease or complete control.

The conidia employed as the inoculum for the test were obtained from recently infected leaf tissue stored in a chillroom at 5° C. The conidia were washed off the leaf surface with a brush and suspended in deionized water. The suspension was sprayed on leaf surfaces with a DeVilbiss atomizer.

In each test, two non-treated control leaves were sprayed with water containing the solvent-surfactant system. In addition, one leaf was sprayed with the commercial fungicide, manganese ethylene-1,2-bisdithiocarbamate (maneb).

The results obtained with a number of compounds of this invention are summarized in the following table. A wide range of concentrations of the test compounds was employed. A blank space in the table indicates that the compound was not tested at the indicated concentration. An asterisk indicates that the compound was phytotoxic at the indicated concentration. When a compound was tested more than once at the same concentration, the result given is an average. The 3-cyanamino compounds were tested as the triethylamine salt. Testing of 3-cyanamino-N,N-diethyl-2,6-dinitro-4-trifluoromethylaniline as the triethylamine salt and the free compound showed both forms performed essentially the same.

TABLE 1

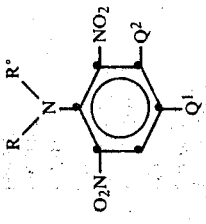

| Q¹ | Q² | R | R° | 800 | 400 | 200 | 100 | 50 | 25 | 12.5 |
|---|---|---|---|---|---|---|---|---|---|---|
| | | | | Downy Mildew Control (ppm.) | | | | | | |
| CF₃ | H | H | n-C₃H₇ | 4 | 3− | 1 | | | | |
| CF₃ | H | H | CH(CH₃)CH(CH₃)C₂H₅ | 4+ | 2+ | 1 | | | | |
| CF₃ | H | H | CH(CH₃)CH₂CH(CH₃)C₂H₅ | 3 | 3− | 3 | | | | |
| CF₃ | H | H | CH(CH₃)CH₂CH₂CH(CH₃)₂ | 2 | 2+ | 1 | | | | |
| CF₃ | H | H | n-C₅H₁₁ | 3+ | 1 | 1 | | | | |
| CF₃ | H | H | n-C₆H₁₃ | 4+ | 2 | 2 | | | | |
| CF₃ | H | H | CH₂CH(CH₃)₂ | 3+ | 1 | 2+ | | | | |
| CF₃ | H | H | CH(CH₃)C₂H₅ | 1 | 2 | 3 | | | | |
| CF₃ | H | H | CH(CH₃)C₅H₁₁ | 2 | 3− | 2+ | | | | |
| CF₃ | H | H | CH(CH₃)C₄H₉ | 5 | 4 | 3+ | | | | |
| CF₃ | H | H | CH(CH₃)C₃H₇ | 3− | 4 | 1 | | | | |
| CF₃ | H | H | CH(C₂H₅)₂ | 4 | 4+ | 2 | | | | |
| CF₃ | H | C₂H₅ | CH(CH₃)CH(CH₃)₂ | 2 | 1 | 3 | | | | |
| CF₃ | H | H | N(C₃H₇)₂ | 2 | 4 | 2+ | | | | |
| CF₃ | H | H | CH₂CH₂CHClCH₃ | 4 | 1 | 2+ | | | | |
| CF₃ | H | H | CH—CH(CH₃)₂ / CH(CH₃)₂ | 1 | | 2 | | | | |
| CF₃ | H | H | CH(CH₃)CH₂OH | 5 | 4+ | 1' | | | | |
| CF₃ | H | H | CH₂—C=CH₂ / CH₃ | 5 | 4+ | 1 | | | | |
| CF₃ | H | [piperidine N—C₂H₅] | N(C₂H₅)₂ 3+ | 5 | 4+ | 1 | 3 | 30+° | | |
| CF₃ | H | H | | 5 | 5 | | | | | |
| CF₃ | H | H | [2,6-dimethylpiperidine, CH₃–N–CH₃] | 5 | 3+ | 3+ | 4 | 4+ | | |

TABLE 1-continued

Structure:

$$\begin{array}{c} R^\circ \\ | \\ R-N-\phantom{x}\text{(phenyl ring with)}\ NO_2,\ Q^2,\ Q^1,\ O_2N \end{array}$$

| Q¹ | Q² | R | R° | \multicolumn{6}{c}{Downy Mildew Control (ppm)} |
|---|---|---|---|---|---|---|---|---|---|
| | | | | 800 | 400 | 200 | 100 | 50 | 25 | 12.5 |
| CF₃ | H | H | ⟨N-piperidinyl with C₂H₅⟩ | 5 | 1 | | | | | |
| CF₃ | H | N-C₃H₇ | n-C₃H₇ | 5 | 5 | 4+ | 3− | 2+1 | | |
| CF₃ | H | n-C₃H₇ | C₂H₄Cl | 5 | 5 | 5 | 4+ | 1 | | |
| CF₃ | H | n-C₃H₇ | cyclopropylmethyl | 5 | 5 | 1+ | 2− | 4− | | |
| CF₃ | Cl | C₂H₅ | methallyl | 1+ | 4 | 1+ | 1 | 1 | | |
| CF₃ | Cl | CH₃ | CH₃ | 5 | 5 | 1+ | 1 | 2− | | |
| CF₃ | Cl | H | CH₃ | 5 | 3 | 3+ | 1 | 1 | | |
| CF₃ | Cl | C₂H₅ | CH(CH₃)OC₂H₅ | 3 | 3+ | 2 | 3+ | 3+ | | |
| CF₃ | Cl | n-C₃H₇ | n-C₃H₇ | * | 3− | 1 | 2 | 1 | | |
| CF₃ | Cl | n-C₃H₇ | methallyl | * | 4+ | 2 | 2 | 2− | | |
| CF₃ | Cl | C₂H₅ | allyl | * | 3− | 4− | 4− | 4+ | | |
| CF₃ | Cl | n-C₃H₇ | methallyl | 4+ | 4+ | 3+ | 3+ | 2− | | |
| CF₃ | Cl | C₂H₅ | n-C₃H₇ | * | 2+ | 4+ | 2+ | 4+ | | |
| CF₃ | Cl | n-C₃H₇ | N(CH₃)₂ | 5 | 2 | 3 | 2 | 4− | | |
| CF₃ | N₃ | C₂H₅ | C₂H₅ | 5 | 5 | 4+ | 5 | 4− | 4 | 2+ |
| CF₃ | N₃ | CH₃ | CH(CH₃)C₂H₅ | 5 | 5 | 4+ | 3− | 2+ | 3− | |
| CF₃ | N₃ | H | CH(CH₃)C₂H₅ | 5 | 4+ | 4+ | 2+ | 4+ | | |
| CF₃ | N₃ | H | CH—CH(CH₃)₂ CH(CH₃)₂ | 4+ | 2 | 3+ | 3− | 5 | | |
| CF₃ | N₃ | H | CH₃ | 5 | 5 | 5 | 4 | 4 | 4− | |
| CF₃ | N₃ | H | CH(C₂H₅)₂ | 5 | 5 | 4 | 5 | 4 | 4 | 3+ |
| CF₃ | N₃ | H | CH(C₂H₅)C₃H₇ | * | 3+ | 4+ | 2 | 2 | 4 | 1+ |
| CF₃ | N₃ | CH₃ | CH₃ | 5 | 5 | 5 | 3 | 2− | | 4− |
| CF₃ | N₃ | C₂H₅ | n-C₄H₉ | 5 | 5 | 4+ | 4 | 2 | 3− | |
| CF₃ | N₃ | C₂H₅ | n-C₃H₇ | 5 | 5 | 5 | 5 | 2 | 4− | 3− |
| CF₃ | N₃ | C₂H₅ | methallyl | 5 | 5 | 5 | 3 | 3 | 3+ | |
| CF₃ | N₃ | n-C₃H₇ | n-C₃H₇ | 5 | 5 | 4+ | 5− | 4+ | 4+ | 3− |
| CF₃ | N₃ | H | N(CH₃)₂ | 5 | 5 | 4 | 2+ | 3+ | 2 | 4+ |
| CF₃ | N₃ | H | CH(CH₃)CONHCH₃ | 3+ | 3− | 3− | | | | |

TABLE 1-continued

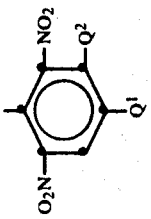

| Q¹ | Q² | R | R° | 800 | 400 | 200 | 100 | 50 | 25 | 12.5 |
|---|---|---|---|---|---|---|---|---|---|---|
| SO₂NHCH₂—N(CH₃)₂-cyclic | H | n-C₃H₇ | n-C₃H₇ | 5 | 5 | 5 | | | | |
| SO₂NH₂ | H | n-C₃H₇ | n-C₃H₇ | 3 | 4 | 2— | | | | |
| SO₂N=S(CH₃)₂ | H | n-C₃H₇ | n-C₃H₇ | 5 | 5 | 5 | 5 | 5 | 4+ | |
| SO₂CH₃ | H | n-C₃H₇ | n-C₃H₇ | 4+ | 4+ | 4+ | 4+ | 4+ | | |
| SO₂N=CHN(CH₃)₂ | H | n-C₃H₇ | n-C₃H₇ | 3 | 1 | 3— | 4— | 4 | 1 | |
| SO₂NHCH₂N-morpholine | H | n-C₃H₇ | n-C₃H₇ | | | 4— | 3 | 3+ | 1 | |
| SO₂N=COCH₃(CH₃) | H | n-C₃H₇ | n-C₃H₇ | | 5 | 4+ | 4 | 3— | 2+ | |
| SO₂N=CHOC₂H₅ | H | n-C₃H₇ | n-C₃H₇ | | | 4+ | 1 | 1 | 1 | |
| SO₂NHCH₂N-morpholine-O | | | | | | | | | | |
| H | Cl | C₂H₅ | C₂H₅ | 5 | 4— | 1— | 1— | 1— | | |
| H | NH₂ | C₂H₅ | C₂H₅ | 5 | 5 | 5 | 4+ | 2+ | | |
| H | OCH₃ | CH₂CH(CH₃)₂ | methallyl | 5 | 4 | 3+ | 4 | 3— | | |
| CH₃ | Cl | CH₂CH(CH₃)₂ | methallyl | 3— | 5 | 3+ | 2— | 4+ | | |
| CH₃ | Cl | n-C₄H₉ | CH(CH₃)CONHCH₃ | 5 | 4+ | 5 | 2+ | 2— | | |
| CH₃ | CH₃ | H | CH(C₂H₅)₂ | 5 | 5* | 4+ | 4 | 4 | 2 | |
| CH₃ | CH₃ | H | CH(C₂H₅)₂ | 5 | 4+ | 3 | 4 | 2— | 2— | |
| H | H | n-C₃H₇ | n-C₃H₇ | 4 | 4+ | 4 | 3— | 3+ | | |
| CH(CH₃)₂ | OCH₃ | H | CH(CH₃)C₂H₅ | 5 | 3+ | 4 | 3— | 1 | | |
| C(CH₃)₃ | OCH₃ | n-C₃H₇ | n-C₃H₇ | 5 | 5 | 3+ | 1 | 3— | 3— | 2+ |
| CF₃ | OCH₃ | C₂H₅ | C₂H₅ | 5 | 3+ | 1 | 1 | 4+ | | |
| CF₃ | OH | C₂H₅ | C₂H₅ | 5 | 5 | 4+ | 4+ | 3 | 1+ | 2— |

TABLE 1-continued

Structure: A benzene ring with N(R)(R°) at position 1, NO₂ at positions 2 and 6 (shown as O₂N and NO₂), Q² at position 3, and Q¹ at position 4.

| Q¹ | Q² | R | R° | 800 | 400 | 200 | 100 | 50 | 25 | 12.5 |
|---|---|---|---|---|---|---|---|---|---|---|
| CF₃ | OCH₃ | H | CH₃ | 4− | 3− | 4+ | 4 | 2+ | 1 | |
| CF₃ | CH₃ | n-C₃H₇ | n-C₃H₇ | 3 | 2 | 1+ | | | | |
| CF₃ | CO₂H | n-C₃H₇ | n-C₃H₇ | 4+ | 3+ | 4− | | | | |
| CF₃ | CONH₂ | H | CH(C₂H₅)₂ | 4− | 3+ | 3+ | | | | |
| CF₃ | CN | n-C₃H₇ | n-C₄H₉ | 5 | 4 | 4 | | | | |
| CF₃ | CONH₂ | C₂H₅ | CH₃ | 5 | 5 | 2− | | | | |
| CF₃ | OCH₃ | CH₃ | CH(C₂H₅)₂ | 5 | 5 | 4+ | 4+ | 3 | 4 | 4+ |
| CF₃ | SCH₃ | H | CH(C₂H₅)₂ | 5 | 5 | 5 | 4+ | 3 | 1+ | 2 |
| CF₃ | SCN | H | CH(C₂H₅)₂ | 5 | 2 | * | 4+ | 1+ | | |
| CF₃ | SCH₂CO₂CH₃ | H | CH₃ | 1+ | 3 | 1 | 3+ | | | |
| CF₃ | SCH₂CH₂CN | C₂H₅ | C₂H₅ | 2 | 3+ | 4 | 2+ | 2− | | |
| CF₃ | SCH₂CN | H | CH₃ | 5 | 4+ | 3+ | 1 | | | |
| CF₃ | SCN | CH₃ | N(CH₃)₂ | 4 | 4 | 4− | | | 2− | |
| CF₃ | SCN | H | n-C₃H₇ | 5 | 4 | 3+ | 2+ | | | |
| CF₃ | SCN | C₂H₅ | C₂H₅ | 3+ | 1 | 1 | 2+ | 1 | | |
| CF₃ | SCH₂CH₂CN | H | CH₃ | 4− | 4− | 2 | 4+ | 1 | 3 | 2+ |
| CF₃ | NHCH₃ | n-C₃H₇ | CH(C₂H₅)₂ | 5 | 5 | 4+ | 2+ | 3 | 1 | 3+ |
| CF₃ | NHCN | H | n-C₃H₇ | 5 | 5 | 4+ | 4 | 4+ | 5 | 4+ |
| CF₃ | NHCN | n-C₃H₇ | CH(C₂H₅)₂ | 5 | 5 | 5 | 5 | 4 | 4− | 3+ |
| CF₃ | NH₂ | C₂H₅ | C₂H₅ | 5 | 5 | 5 | 5 | 5 | 5 | 4+ |
| CF₃ | NH₂ | H | methallyl | 5 | 5 | 5 | 5 | 4+ | 4+ | 3+ |
| CF₃ | NH₂ | CH₃ | CH₃ | 2+ | 1 | 2+ | 4+ | 3− | 3− | |
| CF₃ | NH₂ | H | N(CH₃)₂ | 5 | 4+ | 4+ | 2 | | | |
| CF₃ | NH₂ | H | CH(C₂H₅)C₃H₇ | 2− | 2+ | 3 | 4+ | 4+ | 3 | |
| CF₃ | NH₂ | H | CH(CH₃)C₃H₇ | | 3− | 2+ | 4− | 2+ | | |
| CF₃ | NH₂ | H | N(CH₃)₂ | 5 | 4 | 2+ | | | | |
| CF₃ | H | H | (cyclic: CH₃–CH–N–CH–CH₃) | 4+ | 3 | 4 | | | | |
| CF₃ | NHCN | H | n-C₃H₇ | | 1+ | 2 | 1 | | | |
| SO₂N₃ | H | n-C₃H₇ | n-C₃H₇ | | 5 | 5 | 5 | | | |

TABLE 1-continued

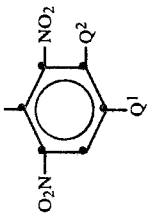

| Q¹ | Q² | R | R° | 800 | 400 | 200 | 100 | 50 | 25 | 12.5 |
|---|---|---|---|---|---|---|---|---|---|---|
| SO₂N(CH₃)OCH₃ | H | n-C₃H₇ | n-C₃H₇ | | 3+ | 3+ | 1 | | | |
| SO₂NH₂ | H | CH₃ | C₂H₅ | | 4+ | 4 | 3+ | | | |
| SO₂NH₂ | H | H | CH(C₂H₅)₂ | | 5 | 5 | 5 | | | |
| SO₂NHNH₂ | H | n-C₃H₇ | n-C₃H₇ | | 4− | 3 | 1 | | | |
| SO₂N(CH₃)₂ | H | n-C₃H₇ | n-C₃H₇ | | 2+ | 2 | 4 | | | |
| SO₂NHCH₃ | H | n-C₃H₇ | n-C₃H₇ | | 3+ | 3 | 3− | | | |
| SO₂NH₂ | H | C₂H₅ | C₂H₅ | | 4+ | 5 | 4 | | | |
| SO₂N(CH₃)OH | H | n-C₃H₇ | n-C₃H₇ | | 4− | 4− | 2 | | | |
| SO₂NHOCH₃ | H | n-C₃H₇ | n-C₃H₇ | | 5 | 5 | 4+ | | | |
| SO₂NH₂ | H | C₂H₅ | methallyl | | 4+ | 4+ | 4+ | | | |
| SO₂NH₂ | H | C₂H₅ | Cl | | 4+ | 5 | 4+ | | | |
| | | | CH₂C=CH₂ | | | | | | | |
| CF₃ | NHCOCH₃ | C₂H₅ | C₂H₅ | 4+ | 4+ | 4 | | | | |
| CF₃ | Cl | H | n-C₃H₇ | 4 | 4+ | 4 | | | | |
| CF₃ | Cl | CH₃ | C₂H₅ | 1 | 1 | 1 | | | | |
| CF₃ | SCN | C₂H₅ | C₂H₅ | 5 | 4− | 1 | | | | |
| CF₃ | NHCN | C₂H₅ | C₂H₅ | | 5 | 4+ | 4+ | | | |
| CF₃ | H | CH₂CH₂Cl | CH₂CH₂Cl | 2+ | 4− | 3− | | | | |
| CF₃ | H | C₂H₅ | CH₂CH₂OH | 5 | 3 | 3− | | | | |
| CF₃ | H | C₂H₅ | CH₂C=CH₂ | 5 | 4+ | 3+ | 1 | | | |
| | | | Cl | | | | | | | |
| CF₃ | H | n-C₃H₇ | CH₂CH=CH₂ | 4− | 2− | 2+ | | 1 | 1 | |
| CF₃ | H | n-C₃H₇ | CH₂CHCH₂ | 5 | 5 | 3+ | 1 | 1 | 4 | |
| | | | O | | | | | | | |
| CF₃ | H | n-C₃H₇ | n-C₃H₇ | 5 | 4+ | 4− | 4+ | 4+ | 4+ | |
| C₂H₅ | | | | | | | | | | |
| SO₂NHCH₂N | H | n-C₃H₇ | n-C₃H₇ | | 5 | 5 | 4+ | 4+ | 4+ | |
| SO₂NHCH₂N | | | | | | | | | 4+ | 3+ |

TABLE 1-continued

| Q¹ | Q² | R | R° | Downy Mildew Control (ppm.) | | | | | | |
|---|---|---|---|---|---|---|---|---|---|---|
| | | | | 800 | 400 | 200 | 100 | 50 | 25 | 12.5 |
| SO₂NHCH₂—C(CH₃)₂-aziridinyl | H | n-C₃H₇ | n-C₃H₇ | | 5 | 5 | 4+ | 5 | 4 | 4+ |
| SO₂NHCH₂-(3-methylpiperidinyl) | H | n-C₃H₇ | n-C₃H₇ | | 5 | 5 | 4 | 4+ | 4+ | 3+ |
| SO₂NHCH₂-(methylpiperidinyl) | H | n-C₃H₇ | n-C₃H₇ | | 3— | 3+ | 4— | | | |
| SO₂N(CH₃)CH₂-(N-methylpiperazinyl) | H | n-C₃H₇ | n-C₃H₇ | | 5 | 4+ | 4+ | 4+ | 4 | 2 |
| SO₂NHCH₂-(morpholinyl) | H | n-C₃H₇ | n-C₃H₇ | | 2+ | 2+ | 4 | | | |
| SO₂NHCH₂-(methylmorpholinyl) | H | n-C₃H₇ | n-C₃H₇ | | 5 | 4+ | 4+ | 5 | 4+ | 4 |
| SO₂NH₂ | H | CH₂CH=CH₂ | CH₂CH=CH₂ | | 4+ | 1 | 1 | | | |
| SO₂N₃ | H | CH₂CH=CH₂ | CH₂CH=CH₂ | | 4+ | 4 | 1 | | | |
| SO₂NHOCH₃ | H | CH₂CH=CH₂ | CH₂CH=CH₂ | | 4+ | 4— | 3+ | | | |
| SO₂N=S(C₂H₅)₂ | H | n-C₃H₇ | n-C₃H₇ | | 2 | 1 | 2 | | | |
| SO₂N=S(CH₃)C₂H₅ | H | n-C₃H₇ | n-C₃H₇ | | 4 | 2 | 4 | | | |
| SO₂NHSC₆H₅ | H | n-C₃H₇ | n-C₃H₇ | | 5 | 5 | 3 | | | |
| SO₂N=S(CH₃)C₆H₅ | H | n-C₃H₇ | n-C₃H₇ | | 4+ | 2+ | 1 | 2— | 2— | |
| SO₂N=S(C₆H₅)₂ | H | n-C₃H₇ | n-C₃H₇ | | 1 | 1 | 4— | | | |
| SO₂N=S(CH₂C₆H₅)₂ | H | n-C₃H₇ | n-C₃H₇ | | 3+ | 2+ | 2+ | | | 2 |

TABLE 1-continued

Structure: Benzene ring with NO₂ (top), O₂N (bottom), Q¹, Q², and N(R)(R°) substituents.

| Q¹ | Q² | R | R° | 800 | 400 | 200 | 100 | 50 | 25 | 12.5 |
|---|---|---|---|---|---|---|---|---|---|---|
| CF₃ | SCN | CH₃ | CH₂-(tetrahydropyran-2-yl) | | 4− | | | | | |
| C(CH₃)₂CN | H | C₂H₅ | C₂H₅ | | 3 | 2− | 3 | | | |
| SO₂N=C(C₂H₅)OC₂H₅ | H | n-C₃H₇ | n-C₃H₇ | | 5 | 5 | 4 | 4+ | 4 | 2+ |
| SO₂N=C(C₆H₅)OCH₃ | H | n-C₃H₇ | n-C₃H₇ | | 4+ | 4+ | 3 | 4+ | 1 | 1 |
| CF₃ | H | CH₂CH=CH₂ | CH₂CH=CH₂ | | 4 | 2 | | | | |
| CH₃ | H | CH₂CH₂CN | CH₂CH₂CN | 4 | 4 | 4− | | | | |
| CH₃ | H | CH₂CH₂Cl | CH₂CH₂Cl | 3− | 3− | 5 | | | | |
| CF₃ | H | CH₂CH₂OH | CH₂CH₂OH | 4 | | | | | | |
| C(CH₃)₂CN | H | n-C₃H₇ | CH(CH₃)C₂H₅ | 4+ | 4+ | 4+ | 4+ | 4+ | 4− | |
| CF₃ | SCN | H | CH₂C≡CH | 5 | 2+ | 3+ | 2+ | | | |
| C(CH₃)₃ | H | n-C₃H₇ | CH₂C(Cl)=CH₂ | 3 | 2− | 4− | 2− | | | |
| CH₂CN | H | n-C₃H₇ | n-C₃H₇ | 4+ | 4− | 4− | 2 | 4 | 3− | 2+ |
| SO₃CH₃ | H | n-C₃H₇ | n-C₃H₇ | | 4+ | 2+ | 4+ | 2− | 1+ | |
| SO₂NH₂ | H | C₃H₇ | cyclopropylmethyl | | 5 | 4+ | 4− | 2+ | 3− | 4− |
| SO₂NH₂ | H | CH₃ | CH(CH₃)C₃H₇ | | 4+ | 4+ | 4 | | | |
| SO₂NH₂ | H | CH₂CH=CH₂ | CH₂C(CH₃)=CH₂ | | 5 | 5 | | | | |
| SO₂NH₂ | H | n-C₃H₇ | CH₂CH(CH₃)₂ | | 5 | 5 | 4 | 2 | 3− | 4 |
| SO₂Cl | NHCN | n-C₃H₇ | n-C₃H₇ | | 4+ | 2 | 1 | | | |
| CF₃ | NHCN | CH₃ | CH₂C≡CH | | 4+ | 4 | 2− | | | |
| CF₃ | NHCN | CH₃ | n-C₃H₇ | | 4+ | 4 | 1 | | | |
| CF₃ | NHCN | n-C₃H₇ | CH₂C(Cl)=CH₂ | | 4 | 1+ | 1 | | | |
| SO₂N(CH₃)SCCl₃ | H | n-C₃H₇ | n-C₃H₇ | | 4− | 3+ | 4− | 1 | 1 | |
| SO₂N=C(CH₃)OC₄H₉ | H | n-C₃H₇ | n-C₃H₇ | | 5 | 5 | 3 | 3− | 1 | 2 |
| SO₂N=C(C₆H₅)OC₂H₅ | H | n-C₃H₇ | n-C₃H₇ | | 5 | 5 | 3 | | | 1 |
| SO₂NHOC₄H₉ | H | n-C₃H₇ | n-C₃H₇ | | 4 | 4 | 3+ | | | |
| SO₂N=C(C₂H₅)OCH₃ | H | n-C₃H₇ | n-C₃H₇ | | 4+ | 5 | 2+ | 1 | 1 | 2 |
| SO₂NH₂ | H | CH₃ | cyclopentyl | 1 | 4+ | 4+ | 3 | 1 | 3− | 1 |
| SO₂NHCH₃ | H | n-C₃H₇ | cyclopropylmethyl | | 2− | 2− | | | | |
| Cl | H | n-C₃H₇ | n-C₃H₇ | 4+ | 3+ | 3− | | | | |

TABLE 1-continued

[Structure: benzene ring with N(R)(R°) substituent, flanked by O₂N and NO₂ groups, with Q¹ and Q² substituents]

| Q¹ | Q² | R | R° | \multicolumn{6}{c}{Downy Mildew Control (ppm.)} |
|---|---|---|---|---|---|---|---|---|---|
| | | | | 800 | 400 | 200 | 100 | 50 | 25 | 12.5 |
| SO₂NHOH | H | n-C₃H₇ | n-C₃H₇ | | 4− | 4+ | 2+ | | | |
| SNH₂ | H | n-C₃H₇ | n-C₃H₇ | | 4− | 2+ | 3− | | | |
| SONH₂ | H | n-C₃H₇ | n-C₃H₇ | | 5 | 5 | 5 | | | |
| Br | H | H | CH(C₂H₅)₂ | | 4+ | 4+ | 4+ | | | |
| CF₃ | SCH₃ | H | CH(C₂H₅)₂ | 5 | 5 | 4+ | 4+ | 4+ | | |
| H | SCH₂CN | C₂H₅ | C₂H₅ | | 3− | 2 | 1 | | | |

The following series of tests illustrates the use of this invention to protect plants from late blight. The host plants in these tests were tomatoes growing in field plots, and were naturally infected with late blight (*Phytophthora infestans*).

The compounds used in these tests were formulated as 25 percent wettable powders, and were dispersed for application in water to produce active ingredient concentrations, in ppm., named in the table below. All dispersions were applied at the rate of 1400 liters/hectare.

When the test began, the plants were about 6 weeks old. The test compounds were applied seven times at intervals of about seven days. Disease control was rated four times at 4–5 day intervals, beginning at the end of the series of spray applications.

Late blight incidence in the untreated control plots was 27 percent as the first observation, increasing to over 80 percent at the last observations.

Disease control achieved by the test compounds is reported below as percent control, compared to untreated controls.

$N=C(R^{19})OR^{20}$, or $N(R^{18})CH_2Het$, and both $R^{14}$ and $R^{15}$ are independently ethyl, n-propyl or 2-chloroallyl.

A third class of preferred compounds are those of Formula III and particularly those wherein $R^7$ is hydrogen or cyano. Especially preferred is the compound wherein $R^7$ is hydrogen and both $R^8$ and $R^9$ are ethyl as well as the compound wherein $R^7$ is hydrogen, $R^8$ is hydrogen and $R^9$ is 3-pentyl. Another preferred compound of this group is the one in which $R^7$ is cyano, $R^8$ is hydrogen and $R^9$ is 3-pentyl.

Another group of preferred compounds are those of Formula I wherein $R^1$ is n-propyl and $R^2$ is n-propyl, 2-chloroethyl or cyclopropylmethyl. Another preferred compound is the compound of Formula VIII wherein Q is thiocyanato; $R^{27}$ is hydrogen and $R^{28}$ is 3-pentyl.

In accordance with standard agricultural practices the 2,6-dinitroanilines to be employed in the presently claimed method are preferably employed in liquid, powder or dust compositions containing one or more of the active compounds. In preparing such compositions, the 2,6-dinitroaniline compounds can be modified with one or more of a plurality of additaments including Table 2

$$\begin{array}{c} R' \quad R'' \\ \diagdown \diagup \\ N \\ | \\ O_2N - \bigcirc - NO_2 \\ | \\ SO_2 \\ | \\ Q' \end{array}$$

| Q' | R' | R'' | | Late Blight Control Observation | | | |
|---|---|---|---|---|---|---|---|
| | | | | 1st | 2nd | 3rd | 4th |
| NHCH₂N (morpholine ring) | n-C₃H₇ | n-C₃H₇ | 50 | 80 | 58 | 52 | 23 |
| | | | 100 | 89 | 59 | 56 | 33 |
| | | | 300 | 90 | 79 | 77 | 47 |
| N=C(CH₃)OCH₃ | n-C₃H₇ | n-C₃H₇ | 50 | 72 | 48 | 23 | 30 |
| | | | 100 | 90 | 78 | 67 | 40 |
| | | | 300 | 87 | 80 | 82 | 77 |
| N₃ | n-C₃H₇ | n-C₃H₇ | 50 | 70 | 52 | 19 | 47 |
| | | | 100 | 90 | 74 | 63 | 65 |
| | | | 300 | 74 | 72 | 67 | 70 |
| NH₂ | n-C₃H₇ | n-C₃H₇ | 50 | 78 | 67 | 52 | 68 |
| | | | 100 | 70 | 77 | 68 | 65 |
| | | | 300 | 91 | 83 | 84 | 67 |
| NH₂ | n-C₃H₇ | C₂H₅ | 50 | 65 | 57 | 53 | 23 |
| | | | 100 | 77 | 74 | 72 | 53 |
| | | | 300 | 86 | 76 | 72 | 57 |
| NH₂ | CH₂C=CH₂ \| Cl | C₂H₅ | 50 | 86 | 81 | 49 | 43 |
| | | | 100 | 52 | 67 | 65 | 47 |
| | | | 300 | 81 | 80 | 62 | 53 |

As will be noted from the data in the above tables, compounds of Formula II are preferred compounds of this invention. Especially preferred compounds of Formula II are those wherein both $R^4$ and $R^5$ are n-propyl, $R^4$ is hydrogen and $R^5$ is methyl, $R^4$ is hydrogen and $R^5$ is 3-pentyl.

Another preferred group of compounds for use in the method of this invention are the compounds of Formula V. Of the compounds of Formula V, the most preferred compounds are those wherein X is $N_3$, $NH_2$, $CH_3$, organic solvents, petroleum distillates, water or other liquid carriers, surface active dispersing agents and finely divided inert solids. In such compositions, the dinitroaniline compound can be present in a concentration from about 2 to 98% by weight.

In the preparation of dust compositions, the dinitroanilines can be compounded with any of the finely divided solids such as pyrophyllite, talc, chalk, gypsum and the like. In such operations, the finely divided carrier is ground or mixed with the dinitroaniline or is wet with a solution of the dinitroaniline in a volatile organic solvent. Similarly, dust compositions containing the active compound can be prepared with various solid surface active dispersing agents, such as fuller's earth, bentonite, attapulgite and other clays. Depending upon the proportions of ingredients, these dust compositions can be employed as concentrates and subsequently diluted with an additional solid surface active dispersing agent or with pyrophyllite, chalk, talc, gypsum and the like to obtain the desired amount of active ingredient in a composition adapted to be employed for the control of phytopathogens. Also, such dust compositions can be dispersed in water with or without the aid of dispersing agents to form liquid sprayable mixtures.

The dinitroaniline compounds or a liquid or dust concentrate composition containing the active compound can be incorporated in intimate mixture with surface active dispersing agents, such as nonionic emulsifying agents, to form spray compositions. Such compositions may be employed as such or may be dispersed in liquid carriers to form diluted sprays containing the active compound in any desired amount.

Similarly, the active dinitroaniline compounds can be compounded with a suitable water immiscible organic liquid and a surface active dispersing agent to produce emulsifiable concentrates which can be further diluted with water and/or oil to form spray mixtures in the form of oil-water emulsions. Preferred dispersing agents to be employed in these compositions are oil soluble and include the nonionic emulsifiers, such as condensation products of alkylene oxides with phenols, sorbitan esters, complex ether alcohols and the like. Suitable organic liquids which can be employed include petroleum oils and distillates, toluene and synthetic organic oils. The surface active dispersing agents are usually employed in liquid compositions in the amount from 0.1 to 20% by weight of the composition.

The formulation of agricultural chemicals is a well-developed art and those skilled in the art will have no difficulty in preparing formulations of active dinitroaniline compounds for use in the practice of the method of this invention.

The exact concentration of the dinitroaniline compound for use in the control of phytopathogens can vary widely provided that an effective amount is applied to the host plant. The amount which is effective is dependent upon the particular compound employed and the severity of the infection. In general, good results are obtained using liquid compositions containing from about 2,000 to about 10 ppm. of the active compound. When dusts are used, good results are usually obtained with compositions containing from about 0.05 to 5.0% or more by weight of the active compound. Preferably, the compounds are applied at a rate of about 10 g. to about 2 kg. per hectare.

We claim:

1. A method for reducing the incidence and severity of grape downy mildew which comprises applying to the foliage of the host plant a fungicidally-effective amount of a dinitroaniline compound having one of the following formulae:

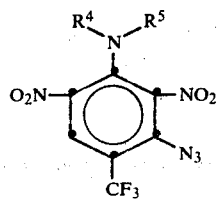

wherein
R$^4$ is H or C$_1$–C$_3$ alkyl;
when R$^4$ is H, R$^5$ is N(R$^6$)$_2$, C$_1$–C$_7$ normal or branched alkyl containing no tertiary carbon atoms, C$_3$–C$_4$ alkenyl or N-methyl-2-propionamido;
when R$^4$ is C$_1$–C$_3$ alkyl, R$^5$ is C$_1$–C$_4$ alkyl or C$_3$–C$_4$ alkenyl; and
each R$^6$ is independently C$_1$–C$_3$ alkyl;

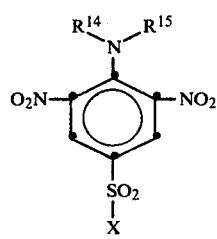

wherein
X is N$_3$;
R$^{14}$ is H, C$_3$–C$_4$ alkenyl or C$_1$–C$_4$ alkyl;
when R$^{14}$ is H, R$^{15}$ is C$_3$–C$_7$ secondary alkyl; and
when R$^{14}$ is not H, R$^{15}$ is C$_1$–C$_5$ alkyl, cyclopropylmethyl, C$_5$–C$_6$ cycloalkyl, C$_3$–C$_4$ alkenyl, halo C$_2$–C$_3$ alkyl or halo C$_3$–C$_4$ alkenyl.

2. A method as in claim 1 wherein the dinitroaniline is a compound of Formula II.

3. The method of claim 2 wherein each of R$^4$ and R$^5$ is n-propyl.

4. The method of claim 2 wherein R$^4$ is hydrogen and R$^5$ is methyl.

5. The method of claim 2 wherein R$^4$ is hydrogen and R$^5$ is 3-pentyl.

6. The method of claim 1 wherein the dinitroaniline is a compound of formula V wherein X is N$_3$ and both R$^{14}$ and R$^{15}$ are n-propyl.

7. A method for reducing the incidence and severity of tomato late blight which comprises applying to the foliage of the host plant a fungicidally effective amount of a dinitroaniline compound of the formula

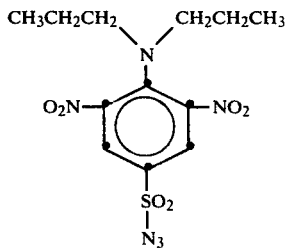

* * * * *

UNITED STATES PATENT AND TRADEMARK OFFICE
CERTIFICATE OF CORRECTION

Page 1 of 2

PATENT NO. : 4,180,568
DATED : December 25, 1979
INVENTOR(S) : James R. Beck, et al.

It is certified that error appears in the above-identified patent and that said Letters Patent are hereby corrected as shown below:

Columns 13 and 14, in Table 1, the 19th compound from the top, in the column headed "200", "1" should be --4+--; in the column headed "100", "3" should be --1--; in the column headed "50", "30+°" should be --3--; in the column headed "25", insert --3+--.

Columns 13 and 14, in Table 1, the 20th compound from the top, in the column headed "R°", delete "3+"; in the column headed "800", "5" should be --3+--; in the column headed "200", insert --5--.

Columns 17 and 18, in Table 1, 6th compound from the top, in the column headed "R°", "n-$C_3C_7$" should read --n-$C_3H_7$--.

Columns 21 and 22, in Table 1, the 22nd compound from the top, in the column headed "R°", insert --n-$C_3H_7$--; under the "Downy Mildew Control (ppm)" heading, move the entire set of numbers one column to the right so that under "800" there is no number; under "400" the number is --5--; under "200" the number is 4+; under "100" the number is 4-; under "50" the number is 4+; under "25" the number is 4+; under "12.5" the number is 4.

UNITED STATES PATENT AND TRADEMARK OFFICE
CERTIFICATE OF CORRECTION

PATENT NO. : 4,180,568

DATED : December 25, 1979

INVENTOR(S) : James R. Beck, et al.

It is certified that error appears in the above-identified patent and that said Letters Patent are hereby corrected as shown below:

Column 29, in Table 2, between the column headings "R'" and "1st", insert the column heading, centered over the column, to read --Concentration--.

Signed and Sealed this

Fourth Day of November 1980

[SEAL]

Attest:

SIDNEY A. DIAMOND

Attesting Officer

Commissioner of Patents and Trademarks